(12) United States Patent
Borch et al.

(10) Patent No.: US 9,670,470 B2
(45) Date of Patent: Jun. 6, 2017

(54) POLYPEPTIDES HAVING PHOSPHOLIPASE A ACTIVITY AND POLYNUCLEOTIDES ENCODING SAME

(71) Applicant: Novozymes A/S, Bagsvaerd (DK)

(72) Inventors: Kim Borch, Birkeroed (DK); Sara Landvik, Vedbaek (DK); Marianne Linde Damstrup, Gentofte (DK); Jesper Brask, Vaerloese (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/777,617

(22) PCT Filed: Mar. 21, 2014

(86) PCT No.: PCT/EP2014/055701
§ 371 (c)(1),
(2) Date: Sep. 16, 2015

(87) PCT Pub. No.: WO2014/147219
PCT Pub. Date: Sep. 25, 2014

(65) Prior Publication Data
US 2016/0289658 A1      Oct. 6, 2016

(30) Foreign Application Priority Data

Mar. 21, 2013  (EP) .................................. 13160387
Apr. 4, 2013   (EP) .................................. 13162328

(51) Int. Cl.
| | |
|---|---|
| *C12N 9/12* | (2006.01) |
| *C12P 7/64* | (2006.01) |
| *C12N 9/20* | (2006.01) |
| *C12N 9/18* | (2006.01) |
| *C11B 3/00* | (2006.01) |

(52) U.S. Cl.
CPC .............. *C12N 9/20* (2013.01); *C11B 3/003* (2013.01); *C12N 9/18* (2013.01); *C12Y 301/01* (2013.01)

(58) Field of Classification Search
CPC ..................................... C12N 9/12; C12P 7/64
See application file for complete search history.

(56) References Cited

U.S. PATENT DOCUMENTS

| | | |
|---|---|---|
| 4,567,046 A | 1/1986 | Inoue |
| 5,264,367 A | 11/1993 | Aalrust |
| 7,713,727 B2 | 5/2010 | Dayton |
| 2004/0063184 A1 | 4/2004 | Grichko |

FOREIGN PATENT DOCUMENTS

| | | |
|---|---|---|
| EP | 0219269 A2 | 4/1987 |
| WO | 2004099400 A2 | 11/2004 |
| WO | 2010124206 A1 | 10/2010 |

OTHER PUBLICATIONS

Andersen et al., UniProt Database, accession No. G3XME8, Dec. 2011.*
Romdhane et al, 2012, Gene, vol. 494, No. 1, pp. 112-118.
Watanabe et al, 1999, Biosci Biotechnol Biochem, vol. 63, No. 5, pp. 820-826.
Waters et al, 2010, J.Agric. Food Chem, vol. 58, No. 12, pp. 7415-7422.
Yang et al, 2006, Food Technol Biotechnol, vol. 44, No. 1, pp. 101-104.
Yang et al, 2009—Uniprot Access No. B8YIE6.
Zhang et al, 2006, Mol Biotech, vol. 33 No. 1, pp. 29-36.
Application sheet Refining of vegetable oils (2004).
Samson et al, Studies in Mycology, vol. 70, pp. 159-183 (2011).
UniprotKB-B8MLJ6 pp. 1-6 (2009).

* cited by examiner

*Primary Examiner* — Maryam Monshipouri
(74) *Attorney, Agent, or Firm* — Kristin McNamara

(57) ABSTRACT

The present invention relates to isolated polypeptides having phospholipase A activity and polynucleotides encoding the polypeptides. The invention also relates to nucleic acid constructs, vectors, and host cells comprising the polynucleotides as well as methods of producing and using the polypeptides.

16 Claims, 2 Drawing Sheets

US 9,670,470 B2

POLYPEPTIDES HAVING PHOSPHOLIPASE A ACTIVITY AND POLYNUCLEOTIDES ENCODING SAME

CROSS-REFERENCE TO RELATED APPLICATIONS

This application is a 35 U.S.C. 371 national application of PCT/EP2014/055701 filed Mar. 21, 2014, which claims priority or the benefit under 35 U.S.C. 119 of European application nos. 13160387.0 and 13162328.2 filed Mar. 21, 2013 and Apr. 4, 2013, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having phospholipase A activity and polynucleotides encoding the polypeptides. The invention also relates to nucleic acid constructs, vectors, and host cells comprising the polynucleotides as well as methods of producing and using the polypeptides.

Description of the Related Art

Phospholipases have been isolated from a wide number of organisms such as animals, plants, bacteria and fungi.

A lipase from *Aspergillus niger* (UNIPROT: B8YIE6) has an amino acid sequence that is 70% identical to the phospholipase of the present invention.

A phospholipase having A1 activity has been made available as LECITASE ULTRA by Novozymes A/S (Yang et al. Food Technol. Biotechnol. 44 (1) 101-104 (2006)).

A number of uses of phospholipases are known in the art, such as to use phospholipase in, e.g. enzymatic degumming of vegetable oil (Yang et al., Supra; U.S. Pat. No. 5,264,367, Metallgesellschaft, Röhm); treatment of starch hydrolysate (particularly from wheat starch) to improve the filterability (EP 219,269, CPC International); as an additive to bread dough to improve the properties of the dough and bread (U.S. Pat. No. 4,567,046, Kyowa Hakko); and for preparation of lyso-lecithin with special emulsifying properties.

Phospholipases may be applied for degumming of vegetable oils to provide refined storage stable vegetable oils of neutral taste and light color suitable for consumption. The degumming process comprises removing the phospholipid compounds also known as phosphatides or "the gum" from the triglyceride rich oil fraction.

Traditionally, the degumming process has been based on water extraction, with acidic or caustic treatment followed by a separation process. Due to the emulsifying properties of the phosphatides, the degumming procedure has resulted in a loss of oil i.e., of triglycerides. However, lately enzymatic degumming has become more widespread. Enzymatic degumming is performed on oils which have been water degummed as well as crude oils. In water degumming of edible oils, a part of the phosphatides is left in the oil. That part is described by the generic term "non-hydratable phosphatides" (NHP). In the production of oils, it is essential to remove the NHP content (U.S. Pat. No. 5,264,367). In the enzymatic degumming process, the NHP are converted by the use of phospholipase into water soluble and water extractable components.

The most widely applied commercial enzyme for industrial degumming of vegetable oils is the phospholipase LECITASE ULTRA from Novozymes A/S (Yang et al., Supra). LECITASE ULTRA has a relatively high thermostability; however, it is most suitable for use in degumming processes at temperatures of up to no more than 55° C.

Enzymatic degumming is generally assisted by the use of acid and caustic chemicals. In the initial degumming step addition of citric acid or phosphoric acid improves hydratability of salt forms of phospholipids by chelating the metals to citrate salts. In the following enzymatic reaction the pH often needs to be partly neutralized (typically by sodium hydroxide addition) to accommodate the pH requirements of the applied enzyme. When using the phospholipase LECITASE ULTRA optimum pH for this reaction is between 5.0 and 5.5 (see application sheet "Refining of vegetable oils—Improving degumming yield"). However, in this pH range, calcium and/or magnesium released during the enzymatic reaction combine with the buffering or chelating acids used to control the reaction conditions, typically leading to salt formation and fouling of equipment with deposits of calcium and magnesium citrate salts (U.S. Pat. No. 7,713,727). It would thus be advantageous if the enzymatic reaction could be performed at a lower pH reducing the need for neutralization of the acid applied.

There is an ever existing need for providing novel phospholipases with improved properties, such as increased activity at high temperature and/or low pH. The present invention relates to such novel polypeptides having phospholipase A activity and polynucleotides encoding the polypeptides.

SUMMARY OF THE INVENTION

The inventors have identified a new polypeptide from *Talaromyces leycettanus* Strain CBS398.68 having phospholipase A activity. The polypeptide of the invention show high thermostability and/or increased activity at elevated temperature. This is an advantage as it allows performing industrial processes at a higher temperature. In enzymatic degumming, the higher temperature may increase the speed of the enzymatic degradation of the phosphatides present in the oil, facilitate the separation of the oil and water phases after the enzymatic degradation of the phosphatides and/or reduce the viscosity of the oil—all of which lead to shorter processing time and higher through-put of the oil refining plant.

Furthermore, the polypeptide of the present invention has a surprisingly high activity at low pH which is an advantage i.a., in enzymatic degumming of vegetable oils where the need for pH adjustment is reduced leading to less buildup of deposits of the process equipment and thus savings from reduced use of chemicals as well as reduced down time for cleaning.

The polypeptides have activity towards the major phospholipids including phosphatidic acid (PA), phosphatidylethanolamine (PE), phosphatidyl inositol (PI), and phosphatidylcholine (PC)

Accordingly, the present invention provides novel polypeptides having phospholipase A activity and polynucleotides encoding the polypeptides.

In a first aspect, the present invention relates to isolated polypeptides having phospholipase A activity selected from the group consisting of: (a) a polypeptide having at least 80% sequence identity to the mature polypeptide of SEQ ID NO: 2 or to the polypeptide of SEQ ID NO: 3; (b) a polypeptide encoded by a polynucleotide that hybridizes under high stringency conditions with (i) the mature polypeptide coding sequence of SEQ ID NO: 1 or the cDNA sequence thereof, or (ii) the full-length complement of (i); (c) a polypeptide encoded by a polynucleotide having at least 65% sequence identity to the mature polypeptide coding sequence of SEQ ID NO: 1 or to the cDNA sequence thereof; (d) a variant of the mature polypeptide of SEQ ID NO: 2 or of the polypeptide of SEQ ID NO: 3 comprising a substitution, deletion, and/or insertion at one or more positions; and (e) a fragment of the polypeptide of (a), (b), (c), or (d) that has phospholipase A activity.

In a second aspect, the present invention relates to an isolated nucleic acid selected from the group consisting of: (a) a nucleotide sequence encoding a polypeptide having phospholipase A activity, wherein said polypeptide comprises the mature polypeptide of SEQ ID NO: 2 or the polypeptide of SEQ ID NO: 3; (b) a nucleotide sequence encoding a polypeptide having phospholipase A activity, wherein said polypeptide comprises an amino acid sequence which has at least 80% identity with the mature polypeptide of SEQ ID NO: 2 or with the polypeptide of SEQ ID NO: 3; (c) a nucleotide sequence encoding a polypeptide having phospholipase A activity, wherein the nucleotide sequence comprises the mature polypeptide coding sequence of SEQ ID NO: 1 or the cDNA sequence thereof; (d) a nucleotide sequence which has at least 80% sequence identity to a nucleotide sequence according to (a), (b), or (c); (e) a nucleotide sequence which hybridizes under high stringency conditions with a complementary strand of a nucleotide sequence according to (a), (b), (c), or (d); (f) a subsequence of a nucleotide sequence according to (a), (b), (c), (d), or (e) having at least 100 nucleotides; (g) a sequence which is degenerate as a result of the degeneracy of the genetic code to a sequence as defined in any one of (a), (b), (c), (d), (e), or (f); and (h) a complementary strand of a nucleotide sequence according to (a), (b), (c), (d), (e), (f) or (g).

In a third aspect, the present invention relates to a nucleic acid construct or expression vector comprising the polynucleotide of the second aspect operably linked to one or more control sequences that direct the production of the polypeptide in an expression host.

In a fourth aspect, the present invention relates to a recombinant host cell comprising the polynucleotide of the second aspect operably linked to one or more control sequences that direct the production of the polypeptide.

In a fifth aspect, the present invention relates to a method of producing the polypeptide of the first aspect, comprising: (a) cultivating a cell, which in its wild-type form produces the polypeptide, under conditions conducive for production of the polypeptide; and (b) recovering the polypeptide.

In a sixth aspect, the present invention relates to a method of producing a polypeptide having phospholipase A activity, comprising: (a) cultivating the host cell of the fourth aspect under conditions conducive for production of the polypeptide; and (b) recovering the polypeptide.

In a seventh aspect, the present invention relates to a composition comprising, (a) the polypeptide of the first aspect or a polypeptide obtainable by the methods of any the fifth or sixth aspects; and (b) optionally a further enzyme.

In an eighth aspect, the present invention relates to a use of the polypeptide of the first aspect or of the composition of any of the seventh aspect, in a process for hydrolysis of phospholipids.

In a ninth aspect, the present invention relates to a method for reducing the content of phosphorus containing components in an edible oil, comprising contacting said oil with an aqueous solution of the polypeptide of any of the first aspect, which is emulsified in the oil until the phosphorus content of the oil is reduced, and then separating the aqueous phase from the treated oil.

DEFINITIONS

Figure 1:
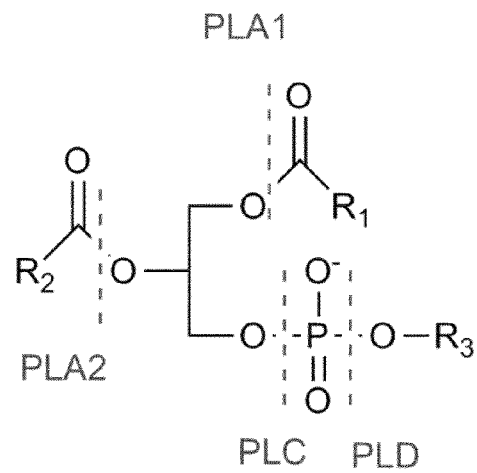
FIG. 1 illustrates where different phospholipases cleave a phospholipid.
Figure 2:
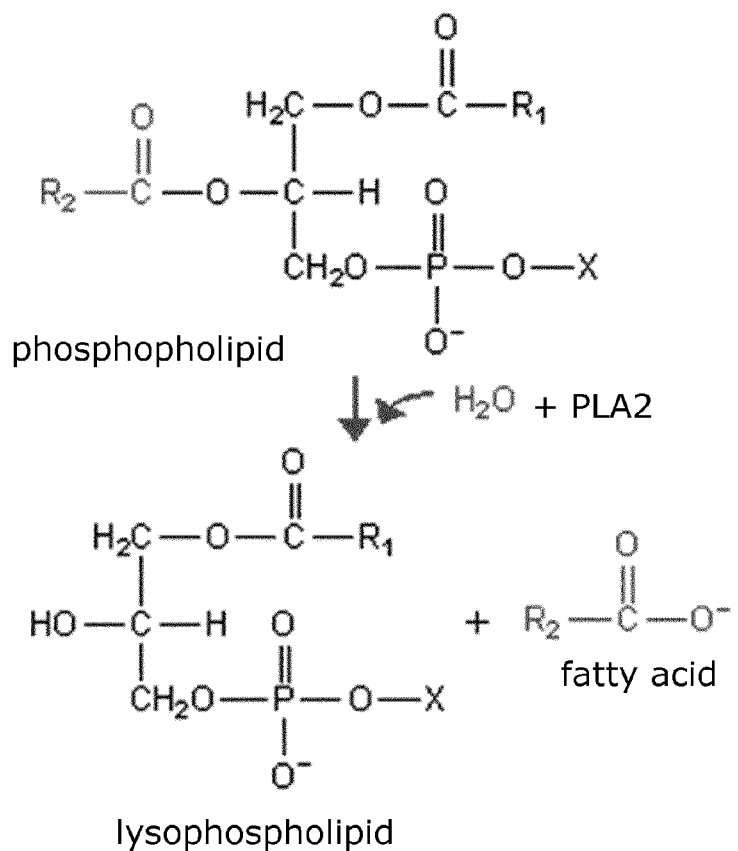
FIG. 2 illustrates the reaction of a phospholipid with a phospholipase A2 to form lysophospholipid with a hydroxyl group at position C2 in the glycerol backbone and a free R2 fatty acid. A similar reaction with phospholipase A1 would cleave of the fatty acid marked with R1 to form a free R1 fatty acid and a lysophospholipid with the hydroxyl group at position C1 in the glycerol backbone.

Phospholipase A activity: In the context of the present invention the term "phospholipase A activity" comprises enzymes having phospholipase A1 and/or phospholipase A2 activity (A1 or A2, EC 3.1.1.32 or EC 3.1.1.4), i.e., hydrolytic activity towards one or both carboxylic ester bonds in phospholipids such as lecithin. A phospholipases having both A1 and A2 activity is also referred to as a phospholipase B.

For purposes of the present invention, phospholipase A activity is determined according to the procedure described in the Material and methods section. In one aspect, the polypeptides of the present invention have at least 20%, e.g., at least 40%, at least 50%, at least 60%, at least 70%, at least 80%, at least 90%, at least 95%, or at least 100% of the phospholipase A activity of the mature polypeptide of SEQ ID NO: 2 and/or of the polypeptide of SEQ ID NO: 3.

In addition to having phospholipase A activity, the polypeptides of the present invention may also have lipase activity.

Phospholipase C activity: Phospholipase C (E.C. 3.1.4.11) removes the phosphate moiety in phospholipids such as lecithin to produce 1.2 diacylglycerol and phosphate ester.

Phospholipase D activity: Phospholipase D (E.C. 3.1.4.4) acts on phospholipids such as lecithin and produces 1,2-diacylglycerophosphate and base group.

Lipase activity: The term "lipase activity" is defined herein as a lipolytic activity which hydrolyses the carboxylic ester bond in glyceryl tributyrate, olein, pNP-butyrate and pNP-palmitate (triacylglycerol lipase, EC 3.1.1.3).

Thermostability: In the context of the present invention the "thermostability" is determined by Differential Scanning calorimetry (DSC) using the method described in Example 1. In one aspect, the polypeptides of the present invention have a denaturation temperature which is at least 5, 6, 7, 8, 9, 10, 11, 12, 13, 14, 15, 16 or even 17° C. higher than the denaturation temperature of LECITASE ULTRA, i.e., of the polypeptide shown in SEQ ID NO: 5.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Crude oil: The term "crude oil" refers to (also called a non-degummed oil) a pressed or extracted oil or a mixture thereof from, e.g. vegetable sources, including but not limited to acai oil, almond oil, babassu oil, blackcurrent seed oil, borage seed oil, canola oil, cashew oil, castor oil, coconut oil, coriander oil, corn oil, cottonseed oil, crambe oil, flax seed oil, grape seed oil, hazelnut oil, hempseed oil, jatropha oil, jojoba oil, linseed oil, macadamia nut oil, mango kernel oil, meadowfoam oil, mustard oil, neat's foot oil, olive oil, palm oil, palm kernel oil, palm olein, peanut oil, pecan oil, pine nut oil, pistachio oil, poppy seed oil, rapeseed oil, rice bran oil, safflower oil, sasanqua oil, sesame oil, shea butter, soybean oil, sunflower seed oil, tall oil, tsubaki oil walnut oil, varieties of "natural" oils having altered fatty acid compositions via Genetically Modified Organisms (GMO) or traditional "breading" such as high oleic, low linolenic, or low saturated oils (high oleic canola oil, low linolenic soybean oil or high stearic sunflower oils).

Degummed oil: The term "degummed oil" refers to an oil obtained after removal of non-hydratable phospholipids, hydratable phospholipids, and lecithins (known collectively as "gums") from the oil to produce a degummed oil or fat product that can be used for food production and/or non-food applications, e.g. biodiesel. In certain embodiments, the degummed oil has the phospholipids content of less than about 200 ppm phosphorus, less than about 150 ppm phosphorus, less than about 100 ppm phosphorus, less than about 50 ppm phosphorus, less than about 40 ppm phosphorus, less than about 30 ppm phosphorus, less than about 20 ppm phosphorus, less than about 15 ppm phosphorus, less than about 10 ppm phosphorus, less than about 7 ppm phosphorus, less than about 5 ppm phosphorus, less than about 3 ppm phosphorus or less than about 1 ppm phosphorus.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has phospholipase A activity. The fragments according to the invention have a size of more than approximately 160 (e.g. amino acids 117-277 of SEQ ID NO: 3), preferably more than 200 amino acid residues, preferably more than 210 amino acid residues, more preferred more than 220 amino acid residues, more preferred more than 230 amino acid residues, more preferred more than 240 amino acid residues, more preferred more than 250 amino acid residues, more preferred more than 260 amino acid residues (e.g., amino acids 18 to 277 or amino acid 1 to 259 of SEQ ID NO: 3), more preferred more than 270 amino acid residues (e.g., amino acids 8 to 277 or amino acid 1 to 270 of SEQ ID NO: 3), and most preferred more than 275 amino acid residues.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 296 of SEQ ID NO: 2 based on the Signal P version 3 program (Nielsen et al., 1997, Protein Engineering 10: 1-6)]. Amino acids 1 to 19 of SEQ ID NO: 2 are predicted as signal peptide. The mature polypeptide is also shown as amino acids 1 to 277 in SEQ ID NO: 3. The N-terminal sequence of the polypeptide expressed in *Aspergillus oryzae* was analyzed using Applied Biosystems Procise protein sequencing system. This showed the following N-terminal sequences:

35 kDa band with the N-terminal DVSSSVL corresponding to residues 28-34 of SEQ ID NO: 2
25 kDa band with the N-terminal EADLDFP corresponding to residues 117-123 SEQ ID NO: 2
25 kDa band with the N-terminal LDFPLTD corresponding to residues 120-126 SEQ ID NO: 2

It is known in the art that a host cell may produce a mixture of two of more different mature polypeptides (i.e., with a different C terminal and/or N terminal amino acid) expressed by the same polynucleotide. It is also known in the art that different host cells process polypeptides differently, and thus, one host cell expressing a polynucleotide may produce a different mature polypeptide (e.g., having a different C terminal and/or N terminal amino acid) as compared to another host cell expressing the same polynucleotide. In one aspect, the mature polypeptide is amino acids 28 to 296 of SEQ ID NO: 2. In another aspect the mature polypeptide is amino acids 117 to 296 of SEQ ID NO: 2 or amino acids 120 to 296 of SEQ ID NO: 2.

Mature polypeptide coding sequence: The term "mature polypeptide coding sequence" means a polynucleotide that encodes a mature polypeptide having phospholipase A activity. In one aspect, the mature polypeptide coding sequence is nucleotides 1 to 1284 of SEQ ID NO: 1 or the cDNA sequence thereof. In one aspect the cDNA sequence comprises or consists of nucleotides 101 to 182, nucleotides 258 to 423, nucleotides 485 to 821, and nucleotides 879 to 1184 of SEQ ID NO: 1. In one aspect the cDNA sequence comprises or consists of nucleotides 1 to 891 of SEQ ID NO: 4. In one aspect the cDNA is nucleotides 58 to 891 of SEQ ID NO: 4. Nucleotides 1 to 57 of SEQ ID NO: 4 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Stringency conditions: Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C. Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C. Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C. Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C. High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C. Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence or the cDNA sequence thereof; wherein the subsequence encodes a fragment having phospholipase A activity.

Variant: The term "variant" means a polypeptide having phospholipase A activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Polypeptides Having Phospholipase A Activity

In an embodiment, the present invention relates to isolated polypeptides having a sequence identity to the mature polypeptide of SEQ ID NO: 2 or to the polypeptide of SEQ ID NO: 3 of at least 75%, at least 80%, at least 85%, at least 90%, at least 91%, at least 92%, at least 93%, at least 94%, at least 95%, at least 96%, at least 97%, at least 98%, at least 99%, or 100%, which have phospholipase A activity. In one aspect, the polypeptides differ by no more than 10 amino acids, e.g., 1, 2, 3, 4, 5, 6, 7, 8, 9, or 10 from the mature polypeptide of SEQ ID NO: 2 or from the polypeptide of SEQ ID NO: 3. In a preferred embodiment the phospholipase A activity is at least 70% of the phospholipase A activity of the polypeptide of SEQ ID NO: 3.

A polypeptide of the present invention preferably comprises or consists of the amino acid sequence of SEQ ID NO: 2, of the amino acid sequence of SEQ ID NO: 3, or of an allelic variant thereof; or is a fragment thereof having phospholipase A activity. In another aspect, the polypeptide comprises or consists of the mature polypeptide of SEQ ID NO: 2 or of the polypeptide of SEQ ID NO: 3.

In a preferred embodiment the polypeptide of the invention is capable of reducing the phosphate content in a crude oil more efficiently than Lecitase Ultra when applied at 70° C. for 2 hours. Preferably, the polypeptide of the invention is capable of reducing the phosphate content to less than 50 ppm phosphorus, preferably less than about 40 ppm phosphorus, more preferably less than about 30 ppm phosphorus, more preferably less than about 20 ppm phosphorus, more preferably less than about 15 ppm phosphorus, more preferably less than about 10 ppm phosphorus, more preferably less than about 7 ppm phosphorus, even more preferably less than about 5 ppm phosphorus, even more preferably less than about 3 ppm phosphorus or most preferably less than about 1 ppm phosphorus.

In a further embodiment the optimal pH range of polypeptide of the present invention is between 1.5 to about 7.0, preferably 2.5 to 6, preferably 3.0 to 5.5, preferably from 3.5 to 5.0 and most preferred from 3.0 to 4.5.

In a further embodiment the polypeptide of the present invention is thermostable. Preferably the thermal denaturation temperature is above 65° C., more preferred above 70° C., even more preferred above 75° C. and most preferred above 80° C. when determined by Differential Scanning calorimetry as described in example 1. In a further embodiment the polypeptide of the present invention is equally thermostable at pH 4 and pH 5, e.g. the DSC value varies less than 5° C., more preferably less than 4° C., even more preferably less than 3° C. and most preferred less than 2° C.

In another embodiment, the present invention relates to an isolated polypeptide having phospholipase A activity encoded by a polynucleotide that hybridizes under high stringency conditions with (i) the mature polypeptide coding sequence of SEQ ID NO: 1 or the cDNA sequence thereof, or (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2, or the polypeptide of SEQ ID NO: 3 or a fragment thereof may be used to design nucleic acid probes to identify and clone DNA encoding polypeptides having phospholipase A activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, or at least 800 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having phospholipase A activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1 or the cDNA sequence thereof; (iii); (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 1 to 100, or nucleotides 1 to 200, nucleotides 1 to 250, or nucleotides 1 to 300 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the present invention relates to an isolated polypeptide having phospholipase A activity encoded by a polynucleotide having a sequence identity to the mature polypeptide coding sequence of SEQ ID NO: 1 or to the cDNA sequence thereof of at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 or of the polypeptide of SEQ ID NO: 3 comprising a substitution, deletion, and/or insertion at one or more (e.g., several) positions. In an embodiment, the number of amino acid substitutions, deletions and/or insertions introduced into the mature polypeptide of SEQ ID NO: 2 or into the polypeptide of SEQ ID NO: 3 is not more than 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for phospholipase A activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Essential amino acids in the sequence of amino acids 1 to 296 of SEQ ID NO: 2 are located at positions H172, D228, and H285. In a preferred embodiment these positions are maintained in the polypeptide of the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Sources of Polypeptides Having Phospholipase a Activity

A polypeptide having phospholipase A activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Nectria*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In another aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide.

In another aspect, the polypeptide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma kon-*

*ingii, Trichoderma longibrachiatum, Trichoderma reesei*, or *Trichoderma viride* polypeptide.

In another aspect, the polypeptide is a polypeptide obtained from *Nectria* sp., e.g., any of *Nectria cinnabarina, Nectria coccinea, Nectria ditissima, Nectria diversispora, Nectria eustromatica, Nectria fofficola, Nectria fragilis, Nectria fuckeliana, Nectria gaffigena, Nectria haematococca, Nectria episphaeria, Nectria magnoliae, Nectria mammoidea* var. *rubi, Nectria mauritiicola, Nectria peziza, Nectria pseudotrichia, Nectria punicea, Nectria radicicola* and *Nectria ramulariae.*

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Nectria*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3- phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Suitable markers for yeast host cells include, but are not limited to, ADE2, HIS3, LEU2, LYS2, MET3, TRP1, and URA3.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and AA/SI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

Examples of origins of replication for use in a yeast host cell are the 2 micron origin of replication, ARS1, ARS4, the combination of ARS1 and CEN3, and the combination of ARS4 and CEN6.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. Preferably the polynucleotide is heterologous, meaning that it does not exist naturally in the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora,* Neocaffimastix, *Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is an *Aspergillus* cell. In a more preferred aspect, the cell is an *Aspergillus oryzae* or *Aspergillus niger* cell. The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Compositions

The present invention also relates to compositions comprising a phospholipase A polypeptide of the present invention with an additional component.

The composition may comprise a phospholipase A polypeptide of the present invention as the major enzymatic component, e.g., a mono-component composition.

The present invention also relates to compositions comprising a mixture of a phospholipase A of the present invention with one or more further phospholipase activities selected from PLA1, PLA2, PLC and PLD.

Alternatively, the composition may comprise additional enzymes, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger*, or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei*, or *Trichoderma viride*.

The compositions may be prepared in accordance with methods known in the art and may be in the form of a liquid or a dry composition. For instance, the composition may be in the form of a granulate or a microgranulate. The polypeptide may be stabilized in accordance with methods known in the art.

The phospholipases of the present invention and compositions comprising these may be formulated with components selected from the group consisting of buffer agents, inorganic salts, solvents, inert solids and mixtures thereof. Appropriate buffer systems, e.g., are made from aqueous solutions of salts or organic acids, amino acids, phosphate, amines or ammonia in concentrations between 0.01 M and 1 M at pH 2 to 10. Preferably, alkali metal salts of citric acid, acetic acid, glycine and/or hydrochlorides of tris (hydroxymethyl}amine and ammonia at 0.1 M to 0.2 M at pH 4 to 8 are used. Preferably, the phospholipase is dissolved in an aqueous buffer solution such as glycine buffer, citric acid buffer, etc. Citrate containing buffers have been found to be very suitable, in particular sodium citrate buffers, preferably at neutral pH.

The compositions of the invention may comprise phospholipases of the invention immobilized unto a solid support. Solid supports useful in this invention include gels. Some examples of gels include Sepharose, gelatin, glutaraldehyde, chitosan-treated glutaraldehyde, albumin-glutaraldehyde, chitosan-Xanthan, toyopearl gel (polymer gel), alginate, alginate-polylysine, carrageenan, agarose, glyoxyl agarose, magnetic agarose, dextranagarose, poly(Carbamoyl Sulfonate) hydrogel, BSA-PEG hydrogel, phosphorylated polyvinyl alcohol (PVA), monoaminoethyl-N-aminoethyl (MANA), amino, or any combination thereof. Another solid support useful in the present invention are resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50, polyvinyl, polyacrylic, polymethacrylate, or any combination thereof. Another type of solid support useful in the present invention is ceramic. Some examples include non-porous ceramic, porous ceramic, SiO2, Ah03. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support. Other exemplary solid supports used to practice the invention comprise diatomaceous earth products and silicates. Some examples include CELITE® KENITE®, DIACTIV®, PRIMISIL®" DIAFIL® diatomites and MICRO-CEL®' CALFLO®, SILASORB™, and CELKA TE® synthetic calcium and magnesium silicates.

Some examples of methods for immobilizing enzymes include, e.g., electrostatic droplet generation, electrochemical means, via adsorption, via covalent binding, via crosslinking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. 0. Kaplan. Volume 136; and Immobilization of Enzymes and Cells. 1997. Humana Press. Edited by G. F. Bickerstaff. Series: Methods in Biotechnology, Edited by J. M. Walker.

Uses

The phospholipase of the invention may be applied in a process for removing phospholipids from an oil, e.g. a vegetable oil, animal oil or fat, tallow, or grease. Applications in which the phospholipase of the invention can be used comprise i) degumming of oil, e.g. vegetable oil, or an edible vegetable oil, in a process comprising hydrolysis of phospholipids in the gum fraction from water degumming to release entrapped triglyceride oil, ii) in a process comprising hydrolysis of phospholipids to obtain improved phospholipid emulsifiers, in particular wherein said phospholipid is lecithin, iii) in a process for improving the filterability of an aqueous solution or slurry of carbohydrate origin which contains phospholipid, iv) in a process for the production of an animal feed product, v) in a process for the production of a biofuel, e.g. a biodiesel, vi) in a process for the production of a detergent product, and/or vii) in a process for making a baked product, comprising adding the phospholipase to a dough, and baking the dough to make the baked product.

Degumming: A phospholipase of the invention may be used for degumming oil, e.g. animal oil or fat, tallow, grease or a vegetable oil, i.e., in a process to reduce the phospholipid content in edible oil. See, for example, WO 2007/103005 and US 2008/0182322. Such a process is applicable to the purification of any edible oil which contains phospholipid, e.g., vegetable oil such as soybean oil, rape seed oil, or sunflower oil or any other oil mentioned under the definition of crude oils.

An aspect of the invention is a method for reducing the content of phosphorus containing components in an edible oil by phospholipase treatment, comprising contacting said oil with an aqueous solution of the polypeptide of the invention under conditions sufficient for the enzymes to react with the phospholipids to form free fatty acid and lysophospholipid products. The lysophopholipid will dissolve in the aqueous phase resulting in reduction of the phosphorus content of the oil. The free fatty acids will stay in the oil. Following the phospholipase treatment the aqueous phase is separated from the treated oil. Phospholipids are commonly measured in oil as "phosphorus content" in parts per million. Table 1 sets forth the typical amounts of phospholipids present in the major oilseed crops, and the distribution of the various functional groups as a percentage of the phospholipids present in the oil.

TABLE 1

Typical levels and phospholipid distributions for common oilseeds

|  | Soy Oil | Canola Oil | Sunflower Oil |
| --- | --- | --- | --- |
| Phosphorus (ppm) | 400-1500 | 200-900 | 300-700 |
| PC % | 12-46 | 25-40 | 29-52 |
| PE % | 8-34 | 15-25 | 17-26 |
| PA % | 17-26 | 10-20 | 15-30 |
| PI % | 2-15 | 2-25 | 11-22 |

The phospholipase treatment can be carried out directly in the crude oil or after removal of slime (mucilage) e.g. by wet refining. In a preferred embodiment the oil is selected from crude oil, water degummed oil, acid degummed oil and caustic refined oil.

After wet refining the oil typically will contain 50-250 ppm of phosphorus as phospholipid at the beginning of the treatment with the phospholipase. In a preferred embodiment of the present invention the treatment reduces the phosphorus value, preferably to below 20 ppm, such as below 15 ppm, such as below 11 ppm, such as to below 10 ppm, below 9 ppm, below 8 ppm, below 7 ppm, below 6 ppm or even 5 below ppm.

The phospholipase treatment is conducted by dispersing an aqueous solution of the phospholipase, preferably as droplets with an average diameter below 10 microM. The amount of water is preferably 0.5-5% by weight in relation to the oil. An emulsifier may optionally be added. Mechanical agitation may be applied to maintain the emulsion. Agitation may be done with a high shear mixer with a tip speed above 1400 cm/s.

In certain embodiments, a suitable oil degumming method comprises a) mixing an aqueous acid with an oil to obtain an acidic mixture having pH of about 1 to 4, b) mixing a base with the acidic mixture to obtain a reacted mixture having pH of about 6-9, and c) degumming the reacted mixture with an enzyme of the present invention to obtain a degummed oil. In certain embodiments, mixing in steps a) and/or b) creates an emulsion that comprises an aqueous phase in average droplet size between about 15 microM to about 45 microM. In certain embodiments, mixing in steps a) and/or b) creates an emulsion that comprises at least about 60% of an aqueous phase by volume in droplet size between about 15 microM to about 45 microM in size, wherein percentage of the aqueous phase is based on the total volume of the aqueous phase. Any acid deemed suitable by one of skill in the art can be used in the methods provided herein. In certain embodiments, the acid is selected from the group consisting of phosphoric acid, acetic acid, citric acid, tartaric acid, succinic acid, and a mixture thereof. Any acid deemed suitable by one of skill in the art can be used in the methods provided herein. In certain embodiments, the base is selected from the group consisting of sodium hydroxide, potassium hydroxide, sodium silicate, sodium carbonate, calcium carbonate, and a combination thereof.

In a preferred embodiment the phospholipase treatment can be conducted at a pH in the range of about 1.5 to about 7.0, preferably 2.5 to 6, preferably 3.0 to 5.5, preferably from 3.5 to 5.0, and most preferred from 3.0 to 4.5. The pH is measured in the emulsion or in the interphase between the oil and aqueous solution. A suitable temperature is generally 30-80° C., (particularly 30-70° C., 40-60° C., e.g., 50-55° C.). In a preferred embodiment the temperature of the oil is between 55 and 80° C., more preferred between 60 and 75° C. and most preferred between 65 and 70° C.

The reaction time will typically be 1-12 hours (e.g., 1-6 hours, or 1-3 hours, most preferred the reaction time is between 1.5 and 4 hours, even more preferred between 1.5 and 2 hours). A suitable enzyme dosage will usually be 0.1-10 mg per liter (e.g., 0.5-5 mg per liter). The phospholipase treatment may be conducted batchwise, e.g., in a tank with stirring, or it may be continuous, e.g., a series of stirred tank reactors. The phospholipase treatment may be followed by separation of an aqueous phase and an oil phase. The separation may be performed by conventional means, e.g., centrifugation. When a liquid lipase is used the aqueous phase will contain phospholipase, and the enzyme may be re-used to improve the process economy.

In addition to the phospholipase of the present invention a further enzyme may be applied in the degumming process outlined above. In a preferred embodiment the further enzyme is a polypeptide having phospholipase A1, A2, B and/or C activity. A suitable polypeptide having phospholipase A1 activity may be LECITASE ULTRA available from Novozymes A/S. A suitable polypeptide having phospholipase C activity may be e.g., the enzyme PURIFINE available from DSM or the PLC's described in WO 2012/062817 and PCT/CN2013/089106.

Phospholipid emulsifiers: The phospholipase of the invention may be used for partial hydrolysis of phospholipids, preferably lecithin, to obtain improved phospholipid emulsifiers. This application is further described in Ullmann's Encyclopedia of Industrial Chemistry (Publisher: VCH Weinheim (1996)), JP patent 2794574, and JP-B 6-087751.

Filtration: The phospholipase of the invention can be used to improve the filterability of an aqueous solution or slurry of carbohydrate origin by treating it with the phospholipase. This is particularly applicable to a solution of slurry containing a starch hydrolyzate, especially a wheat starch hydrolyzate, since this tends to be difficult to filter and to give cloudy filtrates. The treatment can be done in analogy with EP 219,269 (CPC International).

Animal feed: The phospholipase of the invention may be used in a process for the production of an animal feed which comprises mixing the phospholipase with feed substances comprising at least one phospholipid. This can be done in analogy with EP 743 017.

Biodiesel: The phospholipase of the present invention may be used in combination with one or more lipolytic enzymes to convert fats and oils to fatty acid alkyl esters while achieving degumming in the same process. Such a process is for example described in U.S. Pat. No. 8,012,724.

Detergent: The phospholipase of the invention may be added to and thus be used as a component of a detergent composition.

The detergent composition may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

Baking: The phospholipase of the invention may be used for production of dough and baked products from dough, as well as for production of baking compositions and baking additives.

The dough generally comprises wheat meal or wheat flour and/or other types of meal, flour or starch such as corn flour, corn starch, rye meal, rye flour, oat flour, oat meal, soy flour, sorghum meal, sorghum flour, potato meal, potato flour or potato starch.

The dough may be fresh, frozen or par-baked.

The dough is normally leavened dough or dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat is added, and particularly to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin.

The dough may be used for any kind of baked product prepared from dough, either of a soft or a crisp character, either of a white, light or dark type. Examples are bread (in particular white, whole-meal or rye bread), typically in the form of loaves or rolls, French baguette-type bread, pita bread, tortillas, cakes, pancakes, biscuits, wafers, cookies, pie crusts, crisp bread, steamed bread, pizza and the like.

The present invention is further described by the following examples that should not be construed as limiting the scope of the invention.

Material and Methods

Lipolytic Activity (LU)

The lipolytic activity (lipase activity) may be determined using tributyrine as substrate. This method is based on the hydrolysis of tributyrin by the enzyme, and the alkali consumption to keep pH constant during hydrolysis is registered as a function of time.

One Lipase Unit (LU) is defined as the amount of enzyme which, under standard conditions (i.e., at 30° C.; pH 7.0; with 0.1% w/v Gum Arabic as emulsifier and 0.16 M tributyrine as substrate) liberates 1 micromol titratable butyric acid per minute. One KLU is 1000 LU.

Phospholipase A Activity (LEU)

In the LEU assay, the phospholipase A activity is determined from the ability to hydrolyze lecithin at pH 8.0, 40° C. The hydrolysis reaction can be followed by titration with NaOH for a reaction time of 2 minutes. The phospholipase from *Fusarium oxysporum* (LIPOPAN F) disclosed in WO 1998/26057 has an activity of 1540 LEU/mg enzyme protein and may be used as a standard.

Plate Assay
A) Buffers is a mixture of 100 mM HEPES and 100 mM Citrate with pH adjusted from pH 3.0 to pH 7.0.
B) 2% Agarose (Litex HSA 1000) is prepared by mixing and cooking in buffers (A)) for 5 minutes followed by cooling to approximately 60° C.
C) Substrate is L-alfa Phosohatidylcholine, 95% from Soy (Avanti 441601) dispersed in water (MilliQ) at 60° C. for 1 minute with Ultra Turrax.
D) Purified enzyme solutions of LECITASE ULTRA and the mature phospholipase of SEQ ID NO:2 were diluted to 0.4 mg/ml.

Plates were casted by mixing of 5 ml substrate (C)) and 5 ml Agarose (B)) gently mixed into petri dishes with diameter of 7 cm and cooled to room temperature before holes with a diameter of approximately 3 mm were punched by vacuum. Ten microliters diluted enzyme (D)) was added into each well before plates were sealed by parafilm and placed in an incubator at 55° C. for 48 hours. Plates were taken out for photography at regular intervals.

N-Terminal Sequencing Procedure

N-terminal sequencing analyses were performed using an Applied Biosystems Procise® protein sequencing system. The samples were purified on a Novex® precast 4-20% SDS polyacrylamide gel (Life Technologies). The gel was run according to manufacturer's instructions and blotted to a ProBlott® PVDF membrane (Applied Biosystems). For N-terminal amino acid sequencing the main protein band was cut out and placed in the blotting cartridge of the Procise® protein sequencing system. The N-terminal sequencing was carried out using the method run file for PVDF membrane samples (Pulsed liquid PVDF) according to manufacturer's instructions. The N-terminal amino acid sequence can be deduced from the 7 chromatograms corresponding to amino acid residues 1 to 7 by comparing the retention time of the peaks in the chromatograms to the retention times of the PTH-amino-acids in the standard chromatogram.

Enzymes

An enzyme preparation comprising purified enzyme protein of the phospholipase of the invention (TL PLA) which is the mature polypeptide of SEQ ID NO: 2 e.g. amino acids 20 to 296 or 28 to 296 of SEQ ID NO: 2.

A commercial preparation LECITASE ULTRA available from Novozymes. LECITASE ULTRA comprises a protein engineered microbial polypeptide having both triacylglycerol lipase and phospholipase A activity. The polypeptide has the amino acid sequence shown in SEQ ID NO: 5.

Example 1

Characterization of the Enzyme

The thermostability of the phospholipase of the invention was determined by Differential Scanning calorimetry (DSC) using a VP-Capillary Differential Scanning calorimeter (MicroCal Inc., Piscataway, N.J., USA). The thermal denaturation temperature, Td (° C.), was taken as the top of denaturation peak (major endothermic peak) in thermograms (Cp vs. T) obtained after heating enzyme solutions (approx. 0.5 mg/ml) in buffer (50 mM Na-acetate at pH 4.0 or pH 5.0) at a constant programmed heating rate of 200 K/hr.

Sample—and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures were determined at an accuracy of approximately +/−1° C. as 82° C. at pH 4.0 and as 81° C. at pH 5.0.

The polypeptide of SEQ ID NO: 2 when expressed in *Aspergillus oryzae* was identified as having the following N-terminal sequences using the procedure described above:
35 kDa band with the N-terminal DVSSSVL corresponding to residues 28-34 of SEQ ID NO: 2
25 kDa band with the N-terminal EADLDFP corresponding to residues 117-123 SEQ ID NO: 2
25 kDa band with the N-terminal LDFPLTD corresponding to residues 120-126 SEQ ID NO: 2

Figure 3:
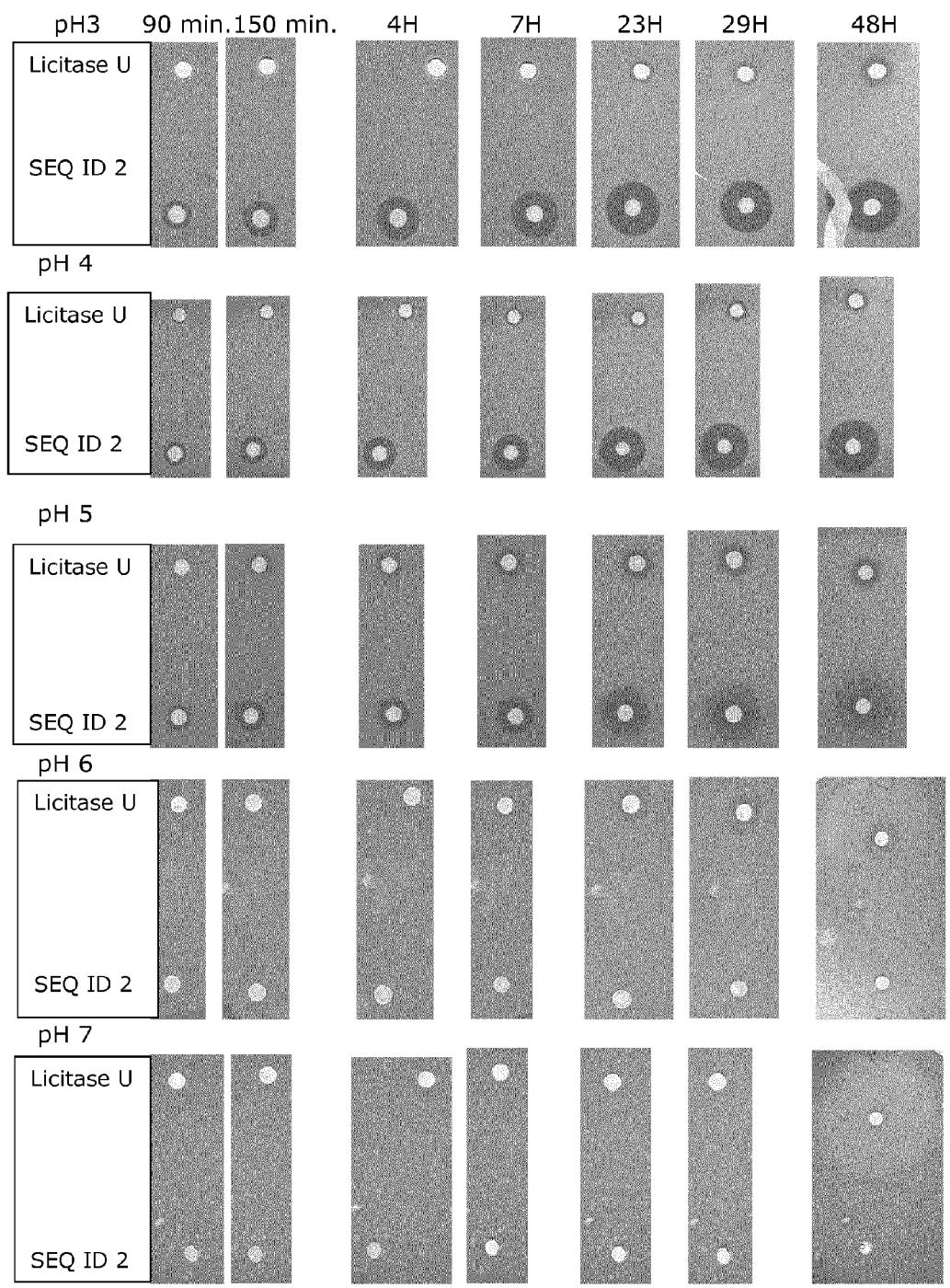
FIG. 3 shows activity on lecithin (PC) plates from pH 3 to pH 7 of Licitase Ultra and the phospholipase of SEQ ID NO: 2. The incubation times were 90 minute, 150 minutes, 4 hours, 7 hours, 23 hours, 29 hours and 48 hours. A dark circle indicates activity, the larger the circle the higher is the activity.

Based on the Plate assay described above the phospholipase of the invention showed activity in the following pH range between 3 and 5. For comparison Lecitase Ultra showed weaker activity at pH 3 and 4 (see FIG. 3).

Example 2

Degumming

Due to the thermostability of the phospholipases applied in commercial enzymatic degumming, the process is usually performed at a temperature of no more than 55° C. However, the phospholipase of the present invention is very thermostable which allows the degumming process to be performed at a higher temperature. In the present example soybean oil was degummed using the phospholipase of the invention or the prior art phospholipase LECITASE ULTRA at a temperature of 70° C.

The oil was initially acid treated with Ortho Phosphoric acid (85% solution) to convert insoluble salts to more hydratable forms and achieve a pH suitable for the enzyme. The acid was applied in amounts equal to 0.05% (100% pure Ortho Phosphoric acid) based on oil amount.

TABLE 2

Characteristics of applied crude soybean oil (pH and mg/kg phosphorous).

|  | pH of oil* | Phosphorous content (mg/kg) |
| --- | --- | --- |
| Crude soybean oil | 6.2 | 840 |
| Crude oil pre-treated with 0.05% Pure Ortho phosphoric acid | 4.0 |  |

*pH in oil was determined by extracting water soluble acids from the oil followed by measurement of the pH of the water phase. To improve the stability of the pH measurement the ionic strength of the water phase was increased by adding 1% w/w KCl.

LECITASE ULTRA was dosed in the amount recommended in the industry 30 mg formulated enzyme product/kg oil=30 ppm), and the phospholipase of the invention was dosed in amounts equal to 34 mg enzyme product/kg oil=34 ppm), 67 mg enzyme product/kg oil=67 ppm), 224 mg enzyme product/kg oil=224 ppm) and 537 mg enzyme product/kg oil=537 ppm.

Aliquots of 250 g crude soybean oil in 500 ml blue cap flasks were heated to 70° C. in water bath with magnetic stirring at 200 rpm. To each flask 87 microliter 85% phosphoric acid solution was applied and the mixture was high shear mixed by Ultra-Turrax at 12.000 rpm for 10 sec. The mixture was hereafter incubated at 70° C. for 15 min and 200 rpm. Enzyme solution and MilliQ-water was applied to a total water addition of 7.5 ml (3% of oil). The mixture was high shear mixed by Ultra-Turrax 12.000 rpm for 10 sec. and incubated at 70° C. for 2 hours with stirring at 200 rpm. After the enzyme reaction, the product mixture was heated by microwave to above 100° C. to inactivate enzyme and facilitate gum separation. Separation of oil and wet gums was achieved by centrifugation at 2000 g for 5 min.

Yield of free fatty acids (FFA) in the degummed oil was quantified by titration. The phosphorous content in the degummed oil was determined by ICP-OES. The results are shown in the table below.

TABLE 3

Average yield of free fatty acids (FFA), and phosphorous as mean of two repeated trials ± standard deviation.

| Sample | FFA content (wt %) | Phosphorous (mg/kg) |
| --- | --- | --- |
| Crude soybean oil | 0.8 ± 0.03 | 840 |
| Blank Control | 0.14 ± 0.00 | 12.5 ± 1.3 |
| LECITASE ULTRA 30 ppm | 0.21 ± 0.05 | 14.1 ± 4.6 |
| Phospholipase of the invention 34 ppm | 0.70 ± 0.01 | 5 |
| Phospholipase of the invention 67 ppm | 0.72 ± 0.06 | 5 |
| Phospholipase of the invention 224 ppm | 0.94 ± 0.12 | 5 |
| Phospholipase of the invention 537 ppm | 1.33 ± 0.22 | 5 |

The highest FFA yield increase and highest phosphorous reduction was achieved with the phospholipase of the invention at pH~4 with 70° C. when compared to Lecitase Ultra.

Example 3

Phospholipase Hydrolysis Measured by Phospholipid Reduction

The phospholipase of the invention and the phospholipase of LECITASE ULTRA were assayed for their ability to hydrolyze the phospholipids phosphatidic acid (PA), phosphatidylethanolamine (PE), phosphatidyl inositol (PI), and phosphatidylcholine (PC) in a low water environment at 50° C. and at 70° C. and pH 4.0 and 5.5. A test substrate was produced from soy bean oil spiked with the phospholipids PA, PE, PI and PC. The substrate comprised 50 mg phospholipids per 1 mL oil. Samples of 250 microliter oil were incubated with the phospholipase of the invention in a thermoshaker at the desired temperature (50 and 70° C.) for 2 h. The phospholipase was applied as 10 microliter of aqueous solution comprising purified enzyme protein in an amount equal to 100 mg/kg oil. Besides the enzymatic reactions, a blank reaction was incubated, in which the enzyme solution was replaced with addition of water.

The samples were analyzed by $^{31}P$ NMR. The principle of the NMR-based assay is that the $^{31}P$ chemical shifts of the phospholipids change after the phospholipids are converted to lyso-phospholipids. The unconverted phospholipids are then quantified by integration. The data is presented as % residual phospholipids relative to the blank reaction.

| Phospholipase of the invention, 50° C. | | |
| --- | --- | --- |
|  | pH 4.0 | pH 5.5 |
| PA | 25 | 0 |
| PE | 27 | 0 |
| PI | 3 | 0 |
| PC | 4 | 0 |

| LECITASE ULTRA, 50° C. | | |
|---|---|---|
| | pH 4.0 | pH 5.5 |
| PA | 12 | 32 |
| PE | 0 | 11 |
| PI | 38 | 18 |
| PC | 14 | 4 |

| Phospholipase of the invention, 70° C. | | |
|---|---|---|
| | pH 4.0 | pH 5.5 |
| PA | 13 | 16 |
| PE | 25 | 33 |
| PI | 19 | 20 |
| PC | 6 | 9 |

| LECITASE ULTRA, 70° C. | | |
|---|---|---|
| | pH 4.0 | pH 5.5 |
| PA | 58 | 18 |
| PE | 68 | 29 |
| PI | 90 | 49 |
| PC | 84 | 20 |

Both enzymes had excellent activity on the phospholipids PA, PE, PI and PC. The highest phosphor reduction was achieved with the phospholipase of the invention which at 50° C. and pH 5.5 reduced the phosphor contend to below the detection limit. At 70° C. and pH 4.0, the phospholipase of the invention showed a surprisingly high activity relative to LECITASE ULTRA.

---

The invention claimed is:

1. A composition comprising a polypeptide having phospholipase A activity and a stabilizing agent, wherein the polypeptide is selected from the group consisting of:
   (a) a polypeptide having at least 90% sequence identity to the mature polypeptide of SEQ ID NO: 2 or to the polypeptide of SEQ ID NO: 3;
   (b) a polypeptide encoded by a polynucleotide having at least 90% sequence identity to the mature polypeptide coding sequence of SEQ ID NO: 1 or to the cDNA sequence thereof; and
   (c) a fragment of the polypeptide of (a) or (b) having more than 160 residues and having phospholipase A activity.

2. The composition of claim 1, wherein the mature polypeptide corresponds to amino acids 28 to 296 of SEQ ID NO: 2 or amino acids 117 to 296 of SEQ ID NO: 2.

3. The composition of claim 1 wherein the polypeptide has at least 95% sequence identity to the mature polypeptide of SEQ ID NO: 2 or to the polypeptide of SEQ ID NO: 3.

4. The composition of claim 1, wherein the polypeptide is encoded by a polynucleotide having least 95% sequence identity to the mature polypeptide coding sequence of SEQ ID NO: 1 or to the cDNA sequence thereof.

5. The composition of claim 1, wherein the polypeptide comprises or consists of SEQ ID NO: 2 or the mature polypeptide of SEQ ID NO: 2, or amino acids 28 to 296 of SEQ ID NO: 2, or amino acids 117 to 296 of SEQ ID NO: 2 or of the polypeptide of SEQ ID NO: 3.

6. A composition comprising,
   1) a polypeptide selected from the group consisting of:
   (a) a polypeptide having at least 90% sequence identity to the mature polypeptide of SEQ ID NO: 2 or to the polypeptide of SEQ ID NO: 3; and (b) a polypeptide encoded by a polynucleotide having at least 90% sequence identity to the mature polypeptide coding sequence of SEQ ID NO: 1 or to the cDNA sequence thereof; and (c) a fragment of the polypeptide of (a) or (b) having more than 160 residues and having phospholipase A activity;

2) a further enzyme; and 3) a stabilizing agent.

7. The composition of claim 6, wherein the further enzyme is an enzyme selected from the group consisting of a phospholipase A1, a phospholipase A2, a phospholipase B and a phospholipase C.

8. A method for reducing the content of phosphorus containing components in an edible oil using phospholipase treatment, comprising contacting said oil with an aqueous solution of a polypeptide, to form a mixture comprising an aqueous phase until the phosphorus content of the oil is reduced, and then separating the aqueous phase from the treated oil, wherein the polypeptide is selected from the group consisting of:

(a) a polypeptide having at least 90% sequence identity to the mature polypeptide of SEQ ID NO: 2 or to the polypeptide of SEQ ID NO: 3; and (b) a polypeptide encoded by a polynucleotide having at least 90% sequence identity to the mature polypeptide coding sequence of SEQ ID NO: 1 or to the cDNA sequence thereof; and (c) a fragment of the polypeptide of (a) or (b) having more than 160 residues and having phospholipase A activity.

9. The method according to claim 8, wherein the oil is selected from crude oil, water degummed oil and acid degummed oil.

10. The method according to claim 8, wherein the temperature of the oil is between 60 and 75° C.

11. The method according to claim 8, wherein the phospholipase treatment is conducted at a pH between 3.0 to 5.5.

12. The composition of claim 1, which is in the form of a liquid or a dry composition.

13. The composition of claim 1, which is in the form of a granulate or a microgranulate.

14. The composition of claim 1, which is immobilized onto a solid support.

15. The composition of claim 6, wherein the polypeptide has at least 95% sequence identity to the mature polypeptide of SEQ ID NO: 2 or to the polypeptide of SEQ ID NO: 3.

16. The method of claim 8, wherein the polypeptide has at least 95% sequence identity to the mature polypeptide of SEQ ID NO: 2 or to the polypeptide of SEQ ID NO: 3.

* * * * *

SEQUENCE LISTING

<160> NUMBER OF SEQ ID NOS: 5

<210> SEQ ID NO 1
<211> LENGTH: 1284
<212> TYPE: DNA
<213> ORGANISM: Talaromyces leycettanus
<220> FEATURE:
<221> NAME/KEY: CDS
<222> LOCATION: (101)..(182)
<220> FEATURE:
<221> NAME/KEY: CDS
<222> LOCATION: (258)..(423)
<220> FEATURE:
<221> NAME/KEY: CDS
<222> LOCATION: (485)..(821)
<220> FEATURE:
<221> NAME/KEY: CDS
<222> LOCATION: (879)..(1181)

<400> SEQUENCE: 1

```
atcgatggaa tgcagaggca agcaaaatcc cagaccgtcc gcctgagctg gtttgcaaaa      60
gttttcatcg gccttttgct cgatcttcaa gactgtcatc atg cac cgt cct ctc      115
                                              Met His Arg Pro Leu
                                              1               5 cag ttg tgg gct ctc gca gcc ctg aca tcg ctg gtc acc gca gct ccg      163
Gln Leu Trp Ala Leu Ala Ala Leu Thr Ser Leu Val Thr Ala Ala Pro
            10                  15                  20 gct cca gtc ctg cgt cgt g gtaaggctca tggaccttgt gccgaactat           212
Ala Pro Val Leu Arg Arg
            25 aaaacaggag cgctgttcat atgcaggtct gactgttaca ttcag at gtg tcc tcg     268
                                                 Asp Val Ser Ser
                                                         30 tct gtc ctg agt gag ctc gat ctc ttc gcg cag tac agt gcg gcc gca      316
Ser Val Leu Ser Glu Leu Asp Leu Phe Ala Gln Tyr Ser Ala Ala Ala
        35                  40                  45 tat tgc tct tcc aac att ggc tcc ccg gga acc aag ttg acg tgc agt      364
Tyr Cys Ser Ser Asn Ile Gly Ser Pro Gly Thr Lys Leu Thr Cys Ser
    50                  55                  60 gtg ggc aat tgc ccc cgg gta gag gct gcg gat acc gag aca tta att      412
Val Gly Asn Cys Pro Arg Val Glu Ala Ala Asp Thr Glu Thr Leu Ile
65                  70                  75 gag ttc aat ga gtaagtgata gacgattccg atcctcgttc cgctctgcac           463
Glu Phe Asn Glu
```

```
                                                                          80
tctctgaaca ccacaatcta g g tct tca tct ttc ggc gac gtt act ggc tac         515
                          Ser Ser Ser Phe Gly Asp Val Thr Gly Tyr
                               85                  90 att gcc gtg gac cga acc aac agc ctg ctc gtt ctg gcg ttc cga ggc           563
Ile Ala Val Asp Arg Thr Asn Ser Leu Leu Val Leu Ala Phe Arg Gly
 95                 100                 105 agt agc act gtc tcc aac tgg gag gca gat ttg gac ttc ccg ttg act           611
Ser Ser Thr Val Ser Asn Trp Glu Ala Asp Leu Asp Phe Pro Leu Thr
110                 115                 120                 125 gat gcc agc agt ctc tgt tcg ggc tgt gaa atc cac agt ggc ttc tgg           659
Asp Ala Ser Ser Leu Cys Ser Gly Cys Glu Ile His Ser Gly Phe Trp
                130                 135                 140 gct gcc tgg cag acg gtt cag gcc agc atc acc tcg acg ctc gag tcg           707
Ala Ala Trp Gln Thr Val Gln Ala Ser Ile Thr Ser Thr Leu Glu Ser
            145                 150                 155 gcc ata gcc agc tat ccc ggc tac acc ctg gtc ttc acc ggc cat agc           755
Ala Ile Ala Ser Tyr Pro Gly Tyr Thr Leu Val Phe Thr Gly His Ser
        160                 165                 170 tat gga gct gcc ttg gct gca atc gcg gcc acg acg ttg cga aat gcc           803
Tyr Gly Ala Ala Leu Ala Ala Ile Ala Ala Thr Thr Leu Arg Asn Ala
    175                 180                 185 gga tac acc atc cag ctg gtaagcgtcc cgccccaacc ataactcttc                  851
Gly Tyr Thr Ile Gln Leu
190                 195 ccgagctcac aacagtccgc gccaaag tat gac tac ggc cag cct cgc ctg ggc         905
                             Tyr Asp Tyr Gly Gln Pro Arg Leu Gly
                                                     200 aat ctg gca ttg gcc cag tac atc acc gcg cag acg caa ggc gcc aac           953
Asn Leu Ala Leu Ala Gln Tyr Ile Thr Ala Gln Thr Gln Gly Ala Asn
205                 210                 215                 220 tac cgc gtc acg cac acc gac gac att gtc ccc aag ctt ccg cct gag          1001
Tyr Arg Val Thr His Thr Asp Asp Ile Val Pro Lys Leu Pro Pro Glu
                225                 230                 235 cta ttt ggc tac cat cat ttc agt ccc gag tac tgg atc acc agt gga          1049
Leu Phe Gly Tyr His His Phe Ser Pro Glu Tyr Trp Ile Thr Ser Gly
            240                 245                 250 gac aat gtg acg gtg acc acc tcc gat gtc caa gtt gtc act ggc atc          1097
Asp Asn Val Thr Val Thr Thr Ser Asp Val Gln Val Val Thr Gly Ile
        255                 260                 265 gac tcg acc gct gga aat gat ggt acg ctt ctc gat agt aca tcg gcg          1145
Asp Ser Thr Ala Gly Asn Asp Gly Thr Leu Leu Asp Ser Thr Ser Ala
    270                 275                 280 cat gac tgg tat att gtc tac atc gac ggg tgc gat taaagaagtc               1191
His Asp Trp Tyr Ile Val Tyr Ile Asp Gly Cys Asp
285                 290                 295 ggcctgcggt atgaatattt ggataaccta cgtatatata tggctccgac gctctaggta        1251
tctagcaaca atataaccct gaggggattt gaa                                     1284

<210> SEQ ID NO 2
<211> LENGTH: 296
<212> TYPE: PRT
<213> ORGANISM: Talaromyces leycettanus

<400> SEQUENCE: 2

Met His Arg Pro Leu Gln Leu Trp Ala Leu Ala Ala Leu Thr Ser Leu
1               5                   10                  15

Val Thr Ala Ala Pro Ala Pro Val Leu Arg Arg Asp Val Ser Ser Ser
            20                  25                  30
```

```
Val Leu Ser Glu Leu Asp Leu Phe Ala Gln Tyr Ser Ala Ala Tyr
        35                  40                  45

Cys Ser Ser Asn Ile Gly Ser Pro Gly Thr Lys Leu Thr Cys Ser Val
 50                  55                  60

Gly Asn Cys Pro Arg Val Glu Ala Ala Asp Thr Glu Thr Leu Ile Glu
 65                  70                  75                  80

Phe Asn Glu Ser Ser Ser Phe Gly Asp Val Thr Gly Tyr Ile Ala Val
                 85                  90                  95

Asp Arg Thr Asn Ser Leu Leu Val Leu Ala Phe Arg Gly Ser Ser Thr
            100                 105                 110

Val Ser Asn Trp Glu Ala Asp Leu Asp Phe Pro Leu Thr Asp Ala Ser
            115                 120                 125

Ser Leu Cys Ser Gly Cys Glu Ile His Ser Gly Phe Trp Ala Ala Trp
    130                 135                 140

Gln Thr Val Gln Ala Ser Ile Thr Ser Thr Leu Glu Ser Ala Ile Ala
145                 150                 155                 160

Ser Tyr Pro Gly Tyr Thr Leu Val Phe Thr Gly His Ser Tyr Gly Ala
                165                 170                 175

Ala Leu Ala Ala Ile Ala Ala Thr Thr Leu Arg Asn Ala Gly Tyr Thr
            180                 185                 190

Ile Gln Leu Tyr Asp Tyr Gly Gln Pro Arg Leu Gly Asn Leu Ala Leu
        195                 200                 205

Ala Gln Tyr Ile Thr Ala Gln Thr Gln Gly Ala Asn Tyr Arg Val Thr
    210                 215                 220

His Thr Asp Asp Ile Val Pro Lys Leu Pro Glu Leu Phe Gly Tyr
225                 230                 235                 240

His His Phe Ser Pro Glu Tyr Trp Ile Thr Ser Gly Asp Asn Val Thr
                245                 250                 255

Val Thr Thr Ser Asp Val Gln Val Val Thr Gly Ile Asp Ser Thr Ala
            260                 265                 270

Gly Asn Asp Gly Thr Leu Leu Asp Ser Thr Ser Ala His Asp Trp Tyr
        275                 280                 285

Ile Val Tyr Ile Asp Gly Cys Asp
        290                 295

<210> SEQ ID NO 3
<211> LENGTH: 277
<212> TYPE: PRT
<213> ORGANISM: Talaromyces leycettanus

<400> SEQUENCE: 3

Ala Pro Ala Pro Val Leu Arg Arg Asp Val Ser Ser Ser Val Leu Ser
1               5                   10                  15

Glu Leu Asp Leu Phe Ala Gln Tyr Ser Ala Ala Tyr Cys Ser Ser
            20                  25                  30

Asn Ile Gly Ser Pro Gly Thr Lys Leu Thr Cys Ser Val Gly Asn Cys
        35                  40                  45

Pro Arg Val Glu Ala Ala Asp Thr Glu Thr Leu Ile Glu Phe Asn Glu
    50                  55                  60

Ser Ser Ser Phe Gly Asp Val Thr Gly Tyr Ile Ala Val Asp Arg Thr
65                  70                  75                  80

Asn Ser Leu Leu Val Leu Ala Phe Arg Gly Ser Ser Thr Val Ser Asn
                85                  90                  95

Trp Glu Ala Asp Leu Asp Phe Pro Leu Thr Asp Ala Ser Ser Leu Cys
```

```
              100                 105                 110
Ser Gly Cys Glu Ile His Ser Gly Phe Trp Ala Ala Trp Gln Thr Val
            115                 120                 125

Gln Ala Ser Ile Thr Ser Thr Leu Glu Ser Ala Ile Ala Ser Tyr Pro
        130                 135                 140

Gly Tyr Thr Leu Val Phe Thr Gly His Ser Tyr Gly Ala Ala Leu Ala
145                 150                 155                 160

Ala Ile Ala Ala Thr Thr Leu Arg Asn Ala Gly Tyr Thr Ile Gln Leu
                165                 170                 175

Tyr Asp Tyr Gly Gln Pro Arg Leu Gly Asn Leu Ala Leu Ala Gln Tyr
            180                 185                 190

Ile Thr Ala Gln Thr Gln Gly Ala Asn Tyr Arg Val Thr His Thr Asp
        195                 200                 205

Asp Ile Val Pro Lys Leu Pro Pro Glu Leu Phe Gly Tyr His His Phe
    210                 215                 220

Ser Pro Glu Tyr Trp Ile Thr Ser Gly Asp Asn Val Thr Val Thr Thr
225                 230                 235                 240

Ser Asp Val Gln Val Val Thr Gly Ile Asp Ser Thr Ala Gly Asn Asp
                245                 250                 255

Gly Thr Leu Leu Asp Ser Thr Ser Ala His Asp Trp Tyr Ile Val Tyr
            260                 265                 270

Ile Asp Gly Cys Asp
        275

<210> SEQ ID NO 4
<211> LENGTH: 891
<212> TYPE: DNA
<213> ORGANISM: Talaromyces leycettanus

<400> SEQUENCE: 4
atgcaccgtc ctctccagtt gtgggctctc gcagccctga catcgctggt caccgcagct    60
ccggctccag tcctgcgtcg tgatgtgtcc tcgtctgtcc tgagtgagct cgatctcttc   120
gcgcagtaca gtgcggccgc atattgctct ccaacattg ctccccggg aaccaagttg    180 acgtgcagtg tgggcaattg ccccggta gaggctgcgg ataccgagac attaattgag    240
ttcaatgagt cttcatcttt cggcgacgtt actggctaca ttgccgtgga ccgaaccaac   300
agcctgctcg ttctggcgtt ccgaggcagt agcactgtct ccaactggga ggcagatttg   360
gacttcccgt tgactgatgc cagcagtctc tgttcgggct gtgaaatcca cagtggcttc   420
tgggctgcct ggcagacggt tcaggccagc atcacctcga cgctcgagtc ggccatagcc   480
agctatcccg gctacaccct ggtcttcacc ggccatagct atggagctgc cttggctgca   540
atcgcggcca cgacgttgcg aaatgccgga tacaccatcc agctgtatga ctacggccag   600
cctcgcctgg gcaatctggc attggcccag tacatcaccg cgcagacgca aggcgccaac   660
taccgcgtca cgcacaccga cgacattgtc cccaagcttc cgcctgagct atttggctac   720
catcatttca gtcccgagta ctggatcacc agtggagaca atgtgacggt gaccacctcc   780
gatgtccaag ttgtcactgg catcgactcg accgctggaa atgatggtac gcttctcgat   840
agtacatcgg cgcatgactg gtatattgtc tacatcgacg ggtgcgatta a            891

<210> SEQ ID NO 5
<211> LENGTH: 274
<212> TYPE: PRT
<213> ORGANISM: Artificial
<220> FEATURE:
```

```
<223> OTHER INFORMATION: Artificial

<400> SEQUENCE: 5

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Ala Asn Leu Asn Phe Trp
                85                  90                  95

Leu Lys Lys Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gln Ala Thr Asp Ala Cys Asn Ala Gly Gly
            260                 265                 270

Phe Ser
```